(12) United States Patent
Juhnke et al.

(10) Patent No.: US 10,184,866 B2
(45) Date of Patent: Jan. 22, 2019

(54) DEVICE AND METHOD FOR TESTING THE MECHANICAL INTEGRITY OF CARTRIDGES FOR LIQUID MEDICAMENTS

(71) Applicant: SANOFI-AVENTIS DEUTSCHLAND GMBH, Frankfurt am Main (DE)

(72) Inventors: Hanno Juhnke, Frankfurt am Main (DE); Jan-Peter Spengler, Frankfurt am Main (DE); Jasmin Groeschke, Frankfurt am Main (DE); Michael Fischer, Frankfurt am Main (DE); Matthias Scharf, Frankfurt am Main (DE); Michael Schrack, Pliezhausen (DE); Olaf Zeckai, Weinheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 29 days.

(21) Appl. No.: 15/502,425

(22) PCT Filed: Aug. 4, 2015

(86) PCT No.: PCT/EP2015/067905
§ 371 (c)(1),
(2) Date: Feb. 7, 2017

(87) PCT Pub. No.: WO2016/020360
PCT Pub. Date: Feb. 11, 2016

(65) Prior Publication Data
US 2017/0227432 A1    Aug. 10, 2017

(30) Foreign Application Priority Data

Aug. 8, 2014 (EP) ..................... 14180351

(51) Int. Cl.
*G01N 3/08* (2006.01)
*G01N 3/12* (2006.01)
*G01M 99/00* (2011.01)

(52) U.S. Cl.
CPC ............ *G01N 3/08* (2013.01); *G01M 99/007* (2013.01); *G01N 3/12* (2013.01); *G01N 2203/0067* (2013.01); *G01N 2203/0274* (2013.01)

(58) Field of Classification Search
CPC ........................................................ G01N 3/08
(Continued)

(56) References Cited

U.S. PATENT DOCUMENTS

| 4,358,961 A * | 11/1982 | Woods, Jr. | ............... | G01N 3/08 73/818 |
| 4,385,643 A * | 5/1983 | Noe | ...................... | F16L 55/136 138/90 |

(Continued)

OTHER PUBLICATIONS

International Preliminary Report on Patentability in International Application No. PCT/EP2015/067905, dated Feb. 14, 2017, 8 pages.

(Continued)

*Primary Examiner* — Lisa Caputo
*Assistant Examiner* — Jamel Williams
(74) *Attorney, Agent, or Firm* — Fish & Richardson P.C.

(57) ABSTRACT

A testing device for testing the mechanical integrity of a hollow breakable item includes a squeezable element to radially abut with a sidewall portion of the breakable item. The testing device further includes a sleeve extending in an axial direction to receive the sidewall portion of the breakable item and having a first contact surface to axially engage with the squeezable element. The testing device also includes a plunger displaceable in axial direction relative to the sleeve and having a second contact surface to axially (Continued)

engage with the squeezable element. The squeezable element is axially squeezable by a relative displacement of plunger and sleeve to increase the squeezable element's radial expansion and to apply radially directed pressure to the breakable item's sidewall portion.

22 Claims, 5 Drawing Sheets

(58) Field of Classification Search
USPC .......................................................... 73/856
See application file for complete search history.

(56) References Cited

U.S. PATENT DOCUMENTS

| | | |
|---|---|---|
| 5,220,824 A | 6/1993 | Shelleman et al. |
| 8,281,818 B1 * | 10/2012 | Vazquez .............. F16L 55/132 |
| | | 138/89 |

OTHER PUBLICATIONS

International Search Report and Written Opinion in International Application No. PCT/EP2015/067905, dated Oct. 23, 2015, 10 pages.

* cited by examiner

DEVICE AND METHOD FOR TESTING THE MECHANICAL INTEGRITY OF CARTRIDGES FOR LIQUID MEDICAMENTS

CROSS-REFERENCE TO RELATED APPLICATIONS

This application is a U.S. national stage application under 35 USC § 371 of International Application No. PCT/EP2015/067905, filed on Aug. 4, 2015, which claims priority to European Patent Application No. 14180351.0 filed on Aug. 8, 2014, the entire contents of which are incorporated herein by reference.

TECHNICAL FIELD

The present disclosure relates to the field of testing cartridges, such like carpules, vials or ampoules that are to be filled with a liquid medicament. In particular, the disclosure relates to detection or determination of the structural integrity of glass cartridges via destructive burst trials.

BACKGROUND

Liquid medicaments, such like insulin or heparin or other liquid medicaments such like vaccines that for instance require administering by way of injection, are typically provided and stored in vitreous cartridges, such like carpules, vials or ampoules. With regard to the type of medicament, the material of the cartridge or container has to be inert. Therefore, cartridges made of glass are nowadays typically used for storing and distributing such liquid medicaments.

Glass cartridges comprising a vitreous body of e.g. cylindrical geometry may become subject to fracture if not handled appropriately. In the event of undue care, glass cartridges may break. Even though in industrial filling and packaging processes, glass cartridges or vitreous bodies thereof are generally handled with due care, occasional breakage of particular cartridges may not be entirely prevented. In case a glass cartridge is damaged, glass splinters may distribute and the medicament contained in the cartridge may contaminate the environment, in particular neighbouring cartridges. In the event, a single glass cartridge is damaged in an industrial manufacturing line, it may become necessary that an entire charge of cartridges has to be visually inspected or discarded at high cost.

In addition, the quality of vitreous barrels or glass cartridges provided form a supplier may be subject to inevitable variations that arise from the glass production or manufacturing process of the respective cartridges.

Macroscopic glass breakage may occur due to a singular or due to repeated impact with a particular force or due to repeated and accumulated enlargement of macroscopic defects, the latter of which are not easily detectable. In typical production processes, a particular glass cartridge may be exposed to a series of low sized mechanical impacts. Any of these impacts alone does not yet lead to a macroscopic glass breakage. But accumulation of successive impact events may constantly lower the cartridge's integrity. This accumulation of mechanical microcracks or mechanical impact can be denoted as glass memory effect.

There exist various methods of testing or determining the glass integrity during or prior to a mass-production or filling process. Typically, the integrity of a vitreous body can be measured with a selection of tools by applying mechanical stress to the glass body from outside with a well-defined force until the glass body breaks or bursts. However, such burst experiments are difficult to control and may not provide sufficiently reproducible results that allow qualitative and quantitative comparison of different charges of cartridges.

SUMMARY

In certain aspects, a method to determine and to test the mechanical integrity of vitreous bodies, e.g., of glass cartridges for a mass-production process, is provided. The method can provide an improved reproducibility of testing parameters allowing to characterize the mechanical integrity of glass cartridges. In some aspects, the accuracy and reproducibility of mechanical stress and impact to be applied to a series of cartridges are improved. In addition, a testing device is provided by way of which the mechanical integrity of breakable items in general and in particular of vitreous cartridges can be tested and inspected with a high degree of reproducibility.

Certain aspects are related to a testing device for testing the mechanical integrity of a hollow breakable item, in particular of a vitreous barrel of a cartridge to be filled with a liquid medicament. The testing device is generally applicable and designed to test the mechanical integrity of different kinds of hollow breakable items and is not generally limited to vitreous items. It is equally applicable to test the mechanical integrity of items made of or comprising a ceramic material, a plastic material, fiber-based materials, metals and combinations thereof.

The testing device comprises a squeezable element to radially abut and/or to radially engage with a sidewall portion of the breakable item. By means of the squeezable element, radially-directed pressure is applicable to the sidewall portion and hence to the breakable item. The testing device further comprises a sleeve extending in an axial direction to receive the sidewall portion of the breakable item. The sleeve further has a first contact surface to axially engage with the squeezable element. The first contact surface of the sleeve typically extends in a plane formed by a radial and tangential direction if the sleeve is considered to be of cylindrical shape. Hence, the plane of the first contact surface typically extends substantially perpendicular to the axial direction or to the elongation of the sleeve.

The testing device further comprises a plunger that is displaceable in axial direction, that is, in a direction parallel to the longitudinal extension of the sleeve. The plunger is displaceable in axial direction relative to the sleeve. The plunger has a second contact surface to axially engage with the squeezable element. Also the second contact surface extends in a plane substantially perpendicular to the axial direction. Typically, first and second contact surfaces extend parallel with respect to each other in order to axially squeeze the squeezable element therebetween. Moreover, the squeezable element, which is typically arranged axially between first and second contact surfaces of sleeve and plunger, respectively, is axially squeezable by a relative axial displacement of plunger and sleeve. Through an axial squeezing of the squeezable element induced by the axial displacement of plunger and sleeve relative to each other the squeezable element's radial expansion increases in order to apply radially-directed pressure to the breakable item's sidewall portion.

In this way, the squeezable element acts as a pressure or force transfer member to redirect and to transfer an axial displacement of plunger and sleeve relative to each other into a force, load or pressure radially acting on the breakable item's sidewall portion.

The squeezable element typically comprises a predefined elasticity and an inherent restoring force acting against a displacement of plunger and sleeve when the squeezable element is axially sandwiched therebetween. The radial abutment of squeezable element and sidewall portion of the breakable item is of particular benefit to apply reproducible and highly reliable mechanical stress or load and hence to apply respective mechanical test conditions to the hollow breakable item. The elasticity and deformability of the squeezable element allows to induce a radially-directed pressure or force into the breakable item's sidewall portion with a comparatively large degree of homogeneity.

Depending on the degree of elasticity or deformability the squeezable element effectively clings or adapts to uneven or bumpy sections of the breakable item's sidewall portion that might be inevitable due to the breakable item's production process. It has to be noted here, that the dimensions of uneven or bumpy sections of the breakable item's sidewall portion are located within a microscopic domain. They may be as small as only a few micrometers or even nanometers since even small sized and particularly tiny bumps or uneven sections of the breakable item's sidewall portion may cause point loads or stress that may lead to premature breakage of the breakable item.

When subject to a testing pressure or force it is of particular benefit, that pressure or force to be applied to the breakable item is exclusively transferred from plunger and/or sleeve only through the squeezable element to the breakable item's sidewall portion. Since a testing force or testing pressure is exclusively transferred to the breakable item via the squeezable element, application of a testing force or testing pressure to the breakable item can be effectively homogenized across the mutual contact surface of the squeezable element and the breakable item's sidewall portion. In this way, detrimental effects on the reproducibility of test results that arise from microscopical bumps or uneven surface portions of the sidewall portion can be effectively compensated.

In various embodiments the testing device is adapted and configured for testing the mechanical integrity of cylindrically-shaped breakable items. In this case, the squeezable element is adapted to radially abut along a ring or annular-shaped section of the sidewall of the breakable item. By making use of the squeezable element, a testing force or testing pressure can be equally and homogeneously applied across the mutual contact surface of squeezable element and breakable item's sidewall portion. In this way, the influence of any local defects of the sidewall structure of the breakable item on the reproducibility or precision of testing or measurement results can be effectively decreased. Consequently, the reproducibility and precision of test results obtained by the testing device can be improved.

The squeezable element is particularly configured and designed to transfer and to homogenize a driving force or pressure induced by the relative motion of plunger and sleeve into a radially-directed pressure, load or force effect acting on the sidewall portion of the breakable item. Any pressure or force effect acting on the breakable item's sidewall portion is then due to an evasive action or movement based on the deformable or elastic properties and the elastic behavior of the squeezable element. The transfer of driving forces or testing pressure to act on the breakable item's sidewall portion can be modified by way of selecting squeezable elements exhibiting varying elastic or plastic properties. Moreover, by making use of squeezable elements of different shape or geometry the radially acting response of a respective squeezable element to a squeezing effect applied by the relative axial movement of plunger and sleeve can be modified accordingly. Hence, the overall deformability and/or elastic properties of the squeezable element may be adapted in accordance to the breaking behavior of the breakable item.

According to a further embodiment the sleeve comprises an axial through opening through which the plunger extends in axial direction. Typically, the sleeve's axial through opening extends through the entire axial elongation of the sleeve. Hence, the sleeve surrounds at least a portion of the plunger, which extends or axially intersects the sleeve. The sleeve is typically of tubular or cylindrical shape and comprises a distal or lower end and a proximal or upper end opposite to the lower or distal end. For squeezing of the squeezable element between first and second contact surfaces of sleeve and plunger either the sleeve is axially fixed while the plunger is axially displaceable relative to the sleeve or the plunger is fixed while the sleeve is axially displaceable relative to the plunger.

It is also conceivable, that for squeezing of the squeezable element both, sleeve and plunger are axially displaceable relative to a mount or base of the testing device. Typically, both, sleeve and plunger at least in sections are of tubular or cylindrical shape. Correspondingly, also the squeezable element arranged between first and second contact surfaces of sleeve and plunger comprises an annular or tubular shape so that a rather homogeneous squeezing thereof is achievable.

Since the plunger extends in axial direction through the sleeve, the sleeve also axially guides the plunger. Typically, the outer diameter of the plunger corresponds and mates with an inner diameter of the sleeve, so that the plunger is guided by the sleeve in axial as well as in radial direction. In this way, the sleeve also acts and serves as a linear guiding for the plunger. It is therefore conceivable, that the plunger is exclusively guided by the sleeve, so that additional guiding means for the plunger become superfluous.

According to a further embodiment the plunger comprises an axially extending shaft portion and a head portion at a shaft portion's distal end. The head portion is radially widened compared to the shaft portion. Typically, it is the shaft portion of the plunger that is axially guided by the sleeve and that comprises an outer diameter that matches and corresponds with the inner diameter of the sleeve. Typically, the shaft portion of the plunger comprises an outer diameter that is slightly less or smaller than the inner diameter of the sleeve so that a smooth axial displacement or guiding of plunger and sleeve can be attained.

The radially-widened head portion comprises an outer diameter that is typically larger than the inner diameter of the sleeve. In this way the head portion protrudes from a distal or lower end of the sleeve. Head portion and the distal end of the sleeve may almost axially abut in order to axially squeeze the squeezable element therebetween. The radially-widened head portion, which is typically also of tubular or cylindrical or disc-like shape serves as an axial abutment for the squeezing element so that mutual axial displacement of plunger and sleeve can be limited at least in one axial direction. Typically, a proximally-directed displacement of the plunger relative to the sleeve can be locked and delimited by the radially-widened head portion getting in abutment with a distal or lower end of the sleeve with the squeezable element axially sandwiched therebetween.

According to a further embodiment the outer surface of the head portion axially flushes with an outer surface of the sleeve. Hence, the outer diameter of the head portion of the plunger is substantially equal to the outer diameter of the sleeve. In this way, both head portion and sleeve exhibit the same or equal radial dimensions, which allows, that both, sleeve and head portion of the plunger are enabled to receive the hollow breakable item. Typically, the hollow breakable item, e.g. of cylindrical shape, can be fitted and put over the arrangement of plunger and sleeve in a way, that a tiny but distinct radial gap remains between an inner face of the sidewall portion of the breakable item and an outer face of sleeve and/or plunger's head portion. In order to insert sleeve and plunger in a contactless way into the hollow breakable item it is of particular benefit, when outer surfaces of the plunger's head portion and the sleeve axially flush.

According to another embodiment the first contact surface is located at a distal end of the sleeve while the second contact surface is located at a proximal face of the plunger's head portion. Typically, the first contact surface is provided by a front face or front side of the sleeve's distal or lower end while the second contact surface located at the plunger is provided and formed by a recessed portion in a transition region of the plunger's head portion and shaft portion.

Since the plunger's shaft portion's diameter substantially mates and matches with the inner diameter of the sleeve and since the outer diameters of the plunger's head portion and the sleeve mutually match, the radial dimensions and size of that section of the head portion radially extending from the shaft portion substantially matches and equals the radial thickness of the sleeve. Consequently, the radial dimensions and/or the overall size of first and second contact surfaces provided at the sleeve's distal end and at the head portion's proximal face are substantially equal.

Having first and second contact surfaces of almost equal size is of particular benefit for axially and tangentially homogeneously squeezing the squeezable element in order to induce a rather homogeneous radially-outwardly directed expansion of the squeezable element along its outer circumference.

It is also of particular benefit, that first and second contact surfaces of sleeve and plunger, respectively, are arranged and aligned substantially parallel and that during mutual axial displacement of plunger and sleeve first and second contact surfaces also remain substantially parallel with respect to each other. This can be attained by means of the axial guiding of the plunger's shaft portion inside the tubular-shaped sleeve.

The size and geometry of the squeezable element is selected such, that its outer circumference in radial direction is smaller than the outer diameter of head portion and/or of the sleeve when the squeezable element is in a relaxed, i.e. non-squeezed state. Upon axially squeezing of the squeezable element its radial dimension increases to such an extent, that its outer circumference at least slightly protrudes from the outer surfaces of the plunger's head portion and/or of the outer surface of the sleeve. In this way, a radial contact and a radial force effect or pressure to the breakable item's sidewall portion is exclusively transferable via the squeezed squeezable element. The degree of squeeze-inducible radial expansion of the squeezable element is typically larger than a radial gap size between the outer surfaces of head portion and/or sleeve and an inner face of the breakable item's sidewall portion.

Generally, the radial expansion of the squeezable element is gradually and continuously variable by varying the driving or squeezing force acting in axial direction between the sleeve and the plunger for squeezing of the squeezable element.

According to another embodiment the squeezable element comprises an elastic ring extending around the plunger and being arranged axially between the first contact surface and the second contact surface. Since it is the plunger's shaft portion that extends through the sleeve, the elastic ring is typically mounted around and fitted on the outer circumference of the plunger's shaft portion. In this way, the plunger's shaft portion serves as a mount and a fixing structure for the annular-shaped squeezable element. Typically, in a relaxed or initial state the squeezable element comprises an inner ring diameter that is equal to or slightly smaller than the outer diameter of the plunger's shaft portion. In this way, the squeezable element is easily fittable around the shaft portion's outer circumference.

In an initial configuration, the squeezable element can be put over the plunger's shaft portion until it axially abuts with the head portion's second contact surface. By displacing the plunger in proximal direction relative to the sleeve, the squeezable element may then be brought into axial contact with the first contact surface of the sleeve in order to induce a radial widening and extension of the squeezable element.

The squeezable element typically exhibits a well-defined elastic modulus. Typically, the squeezable element comprises an annular shape and therefore comprises a ring structure, wherein the cross-section of a ring portion may be of arbitrary shape and may be designed and adapted to the requirements in regard to its elastic deformability. The cross-section of the ring portion may either be circular, oval, elliptic or even rectangular or quadratic. It is even conceivable, that not only one but at least two or a series of squeezable elements are arranged axially adjacent between first and second contact surfaces of sleeve and plunger.

The material of the squeezable element may vary in accordance with the requirements in regard to deformability of the squeezable elements and in accordance with a required response to axial stress, force or pressure. Typically, the squeezable element is made of an elastomeric material, such like natural or synthetic rubber. In particular, the squeezable element may comprise at least one of nitrile rubber, nitrile butadiene rubber (NBR), hydrogenated nitrile butadiene, ethylene propylene, ethylene propylene diene monomer rubber (EPDM), natural rubber, cellular rubber, foam rubber, neoprene or polychloroprene rubbers, fluorocarbon rubber, perfluorocarbon rubber, fluoronated hydrocarbon, ethylene-acrylate rubber, polyester urethane, bromo isobutylene isoprene, polybutadiene, chloro isobutylene isoprene, polychloroprene, chlorosulphonated polyethylene, epichlorohydrin, polyether urethane, fluoro silicone, fluorocarbon rubber, polyisoprene, isobutylene isoprene butyl, acrylonitrile butadiene, polyurethane, styrene butadiene, styrene ethylene butylene styrene copolymer, polysiloxane, vinyl methyl silicone, acrylonitrile butadiene carboxy monomer, styrene butadiene carboxy monomer, thermoplastic polyether-ester, styrene butadiene block copolymer, styrene butadiene carboxy block copolymer, silicone, polytetrafluoroethylene (PTFE), foamed polyethylene, thermoplastic elastomers and combinations thereof. Alternatively or additionally the squeezable element may also comprise an annular ring made of spring steel or comparable spring elements. It is even conceivable, that the squeezable element comprises a multilayer structure with a comparatively hard and non-elastic core cladded by or surrounded by a comparatively soft and elastic shell.

According to a further embodiment the sleeve and the plunger axially extend through a holder that has an abutment to axially engage with a proximal end of the breakable item. Typically, sleeve and plunger axially extend downwards from the holder, so that the hollow breakable item is attachable to a downward pointing section of the holder and/or the arrangement of sleeve and plunger from below. In the event of breakage of the breakable item, respective splinters or fragments may simply fall down without getting in contact with the holder and/or with any one of sleeve or plunger. In this way, contamination of the testing device by splinters or fragments of broken breakable items can be effectively prevented.

Since the holder features a downward-facing abutment, a proximal end of the breakable item can be attached to the holder in a well-defined axial position. Since plunger and sleeve will be also arranged in a well-defined axial position relative to the holder, any load-, force- or pressure effect arising from the displacement of sleeve and plunger always enters at the same axial position into the breakable item's sidewall. In this way the abutment of the holder provides a kind of an axial abutment and a mount for the breakable item so that testing of the mechanical integrity of breakable items is always conducted at one and the same axial position of a series of items. In this way, a high degree of testing precision and testing reproducibility is attainable.

According to another embodiment at least the sleeve is axially displaceable relative to the holder. In this way, the axial position of the first contact surface, typically defining an axial abutment for the squeezable element attached to the axially displaceable plunger can be modified in comparison to the axial position of the holder's abutment. Consequently, the axial position of a testing area of the hollow breakable item is modifiable. Typically and additionally the sleeve is axially fixable to the holder at variable axial positions.

The sleeve is continuously or gradually displaceable in axial direction relative to the holder and it is also fixable to the holder not only at discrete axial positions but also at arbitrary non-discrete positions. In other words, the axial position of the sleeve is continuously variable in axial direction relative to the holder and hence relative to the holder's abutment. By axially fixing the sleeve at a given axial position relative to the holder, a series of hollow breakable items can be tested and can become subject to a well-defined mechanical stress or force effect always at the same axial position. Testing results of a series of breakable items are therefore not only reproducible but are also directly comparable.

According to another embodiment the abutment of the holder comprises an annular seal with a distally-facing abutment surface. Typically, the abutment, hence the annular seal is arranged at a distal front face of the holder. The hollow breakable item, which is typically of tubular shape is arrangeable in sealing contact with the abutment and hence with its annular seal so that the interior volume of the hollow breakable item can be effectively sealed in a fluid- or gas-tight manner to the environment. The annular seal typically comprises a sealing material that may comprise a polymeric or elastomeric material, such like synthetic or natural rubber. It is also conceivable that the abutment just comprises a non-sealing abutment material, such like a comparatively hard plastic material.

Furthermore and according to another embodiment the plunger comprises an axial bore to apply a negative pressure to the interior volume of the breakable item. Negative pressure or a vacuum can be effectively applied to the interior volume when the hollow breakable item abuts in a fluid- or gas-tight manner against the annular seal of the holder's abutment. By applying negative pressure or by generating a vacuum to the interior volume of the breakable item, the breakable item can be axially fixed to the holder in a substantially force-free or load-free way.

Moreover, when the annular seal of the abutment comprises a substantially flat and even-shaped sealing surface or abutment surface the hollow breakable item axially attached to the holder and sucked against the annular seal, the breakable item is displaceable in radial direction as long as its proximal end remains in gas- or fluid-tight abutment with the annular seal. By means of the force-free or load-free arrangement and fixing of the hollow breakable item on the basis of a negative pressure inside the breakable item, a substantially force-free or load-free radial centering of the hollow breakable item can be achieved right at the beginning of a radial expansion of the squeezable element.

In the event that an annular gap between the relaxed or non-stressed squeezable element and the inner face of the breakable item's sidewall portion varies in circumferential or tangential direction, the axial fixing of the breakable item through application of negative pressure or vacuum there inside allows for a slight alignment of the breakable item in radial direction relative to the arrangement of sleeve and plunger until the continuously and radially-outwardly expanding squeezable element homogeneously abuts with the inner face of the breakable item.

According to another embodiment the testing device further comprises an actuator to displace the plunger relative to the sleeve. Typically, the plunger is mechanically and directly connected to the actuator while the sleeve is fixed to the holder. By way of the actuator, typically comprising an electrically-driven motor or some other type of displacing arrangement the plunger can be displaced in axial direction relative to the sleeve in a precisely controllable way. The testing device further comprises at least one of a force sensor and a displacement sensor. The force sensor is adapted and configured to determine and to measure an axial driving force present on the plunger while the displacement sensor is operable and designed to determine and axial displacement path of the plunger relative to the sleeve.

By means of the force sensor, a squeezing force applied to the squeezable element can be determined. By way of the displacement sensor, the axial displacement between plunger and sleeve as it is induced by the actuator can be precisely measured or determined. In particular, the testing device comprises both, a force sensor and a displacement sensor. In this way, a force-displacement path diagram can be monitored and recorded during a continuous displacement of the plunger relative to the sleeve. The axial displacement path as well as the corresponding force applied in order to achieve the respective displacement is a direct indicator for the radial force effect axially applied to the sidewall portion of the hollow breakable item.

The at least one of a force sensor and a displacement sensor may be integrated into the actuator. The respective sensors may be based on commonly-known sensor principles. The force sensor may be implemented as an electric force sensor, e.g. on the basis of a piezo crystal while the displacement sensor may be implemented electrically, optically or magnetically. Certain aspects are related to a method of testing the mechanical integrity of a hollow breakable item, in particular of a cartridge filled or to be filled with a medicament, typically with a liquid medicament. The method comprises the steps of arranging the hollow breakable item over an axially-extending sleeve of a testing device, typically of a testing device as described above. The hollow breakable item is arranged in a predetermined axial position relative to the testing device's sleeve. In a further step, a plunger of the testing device is axially displaced relative to the sleeve to axially squeeze a squeezable element between first and second contact surfaces of sleeve and plunger, respectively.

The squeezable element is axially squeezed in order to increase the squeezable element's radial extension to such an extent that the squeezable element applies a radially-directed pressure to a sidewall portion of the breakable item. Typically, the squeezable element is arranged between a proximal-facing second contact surface and a distally-facing first contact surface. The second contact surface is displaced in proximal direction relative to the first contact surface, thereby axially squeezing the squeezable element. Due to its deformability or elasticity the squeezable element becomes subject to a radial deformation, thereby increasing its outer circumference.

Since the sleeve, the plunger as well as the squeezable element are all located inside the hollow breakable item, the lateral or radial expansion of the squeezable element serves to induce a radially-outwardly directed pressure, force effect or stress to a sidewall portion of the breakable item. Through a gradual and continuous increase of the degree of squeezing of the squeezable element, a radial force effect or stress acting on the breakable item's sidewall portion may gradually increase until the breakable item eventually becomes subject to breakage. In this way, the maximum strength and mechanical resistance of the hollow breakable item can be determined and tested. In this way, a rather reproducible and precise approach can be provided in order to test and to determine whether a given hollow breakable item fulfills predefined conditions in terms of mechanical stability and mechanical integrity.

Since the radially directed response to an axial squeezing of the squeezable element is effective on the breakable item's sidewall portion a variety of different and well-defined stress and mechanical load scenarios can be easily implemented by choosing an appropriate squeezable element. The squeezable element inherently provides a force or pressure transfer function. Axially applied pressure may be linearly or non-linearly transferred into a radially-outwardly acting radial pressure or force effect. The axial-radial pressure transfer function may provide specific characteristics, so that radial pressure or radial load can be applied to the breakable item's sidewall portion in a rather fine-tuned and reproducible way. Moreover, the gradient or slope of such a pressure transfer function may depend on the absolute axial pressure applied to the squeezable element. It is also conceivable, that the radial pressure response asymptotically approaches a maximum value so that a further increase of a given axial pressure has only a rather limited or a negligible effect on a further radial expansion of the squeezable element.

In this way and by selecting a squeezable element exhibiting a desired and beneficial axial-radial pressure transfer function, a particular pressure region of interest can be precisely examined and investigated with a high degree of reproducibility.

According to a further embodiment at least one of an axial driving force applied to the plunger and an axial displacement path of the plunger relative to the sleeve is determined by means of at least one of a force sensor and a displacement sensor, respectively, during the axial displacement of the plunger relative to the sleeve. By determining or measuring axial driving force and axial displacement a force-displacement path diagram can be monitored and recorded. The slope and other characteristics of such diagrams provide an indication for the mechanical integrity of the breakable item. Moreover, even varying geometric dimensions of the hollow breakable item can be determined on the basis of such a force-displacement path diagram.

According to another embodiment the driving force is monitored or measured over the relative axial displacement path of plunger and sleeve until the breakable item is actually subject to breakage. The moment of breakage is detectable in such a diagram since the resistance of the hollow breakable item acting against the radially-outwardly directed expansion of the squeezable element abruptly disappears. Consequently, a rather sharp peak or a comparable distinct portion is visible the pressure-displacement path diagram.

Furthermore and according to another embodiment the breakable item is axially fixed to a holder of the testing device. Axial fixing may be conducted by way of applying a negative pressure to the interior volume of the breakable item. Additionally or alternatively it is conceivable, that the breakable item is at least manually and temporarily axially fixed to the holder until the squeezable element is radially expanded to such a degree that it frictionally holds and fixes the breakable item to the holder, thereby also fixing the breakable item axially to the arrangement of sleeve and plunger.

In addition, the breakable item is radially centered with regard to at least any one of the sleeve, the plunger and the holder by means of the radially expanding squeezable element. Irrespective of the way the breakable item is initially axially fixed to the holder it is radially displaceable to a certain extent during a beginning of a radial expansion of the squeezable element. Hence, the breakable item is to be kept in an axially fixed but radially floating configuration so that by way of an increasing radially-outwardly expanding squeezing element an automatic centering and radial alignment of the breakable item may take place with regard to the basic geometry of the squeezable element. In this way, and by radially centering the breakable item with regard to the squeezable element, the sleeve and/or the plunger a homogeneously distributed mechanical load can be applied around the outer circumference of the squeezable element to the sidewall portion of the hollow breakable item.

It is generally to be noted here, that the above described method is particularly adapted to be implemented and conducted by the testing device as described above. Consequently, all effects, benefits and features described in connection with the testing device are equally valid for the method of testing; and vice versa.

The testing device as well as the method of testing are equally applicable to empty breakable items, such like vitreous or glass cartridges adapted to receive and to accommodate liquid medicaments. The testing device and the method are equally applicable to breakable items that are actually filled with a liquid medicament or other pharmaceutical substances.

Displacement of the plunger relative to the sleeve may be conducted quasistatically, hence with a quasistatic increasing load or with varying loading rates. In this way, dynamic effects of the squeezable element may be equally exploited to investigate the mechanical integrity of the hollow breakable item.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, exemplary embodiments are described in detail by making reference to the Figures, in which.

DETAILED DESCRIPTION

Figure 1:
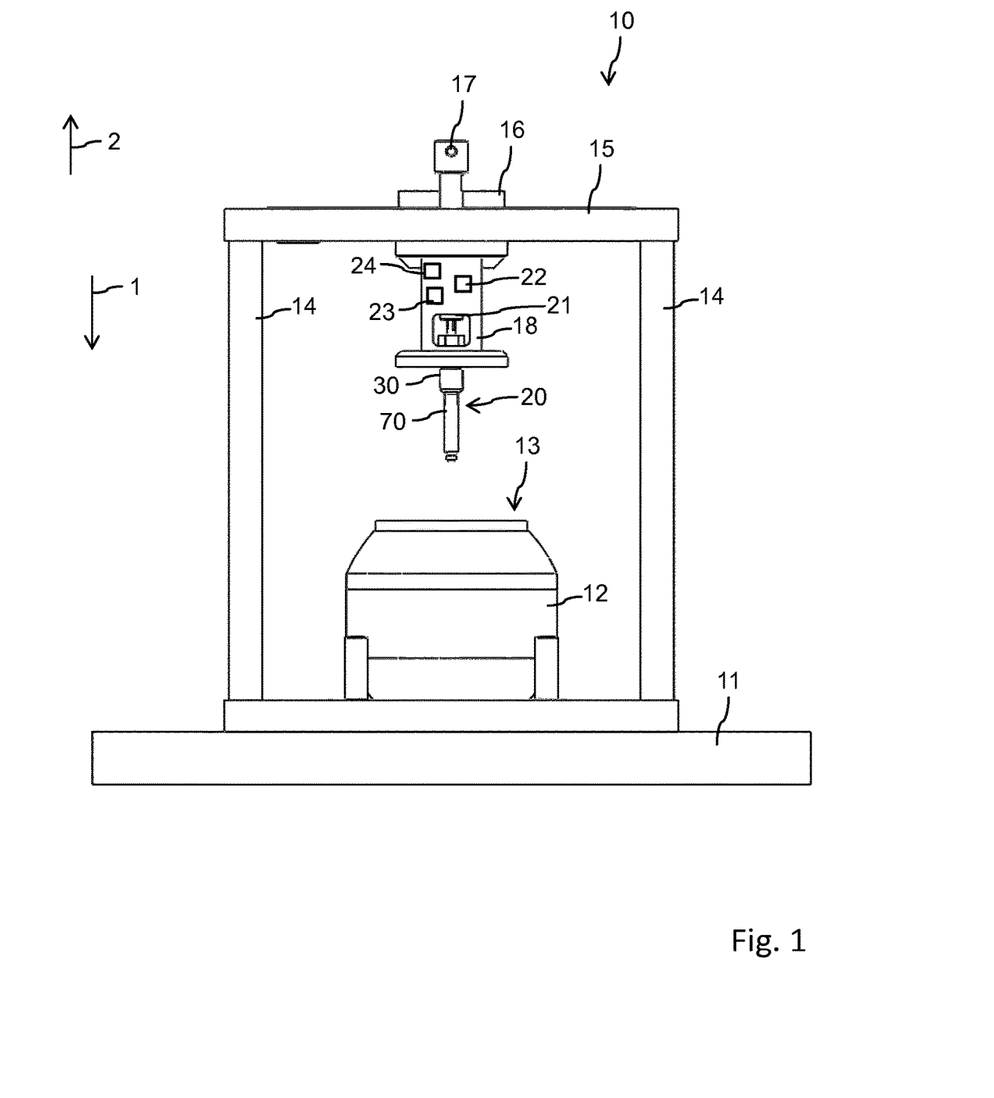
FIG. 1 shows a schematic illustration of a test station comprising a testing device.

In FIG. 1, a test station 10 to conduct a testing of the mechanical integrity of hollow breakable items 70 is schematically illustrated. The test station 10 is particularly adapted to test the mechanical integrity of vitreous tubular barrels 71, such like cartridges that are to be filled with a liquid medicament, such like insulin. The test station 10 as illustrated in FIG. 1 comprises a base 11 having a support 14 to carry and to support a crossbar 15 at which the test device 20 is attached by means of a mount 16. By means of the support 14 the test device 20 is kept in an elevated position relative to the ground or relative to the base 11. In this way, the hollow breakable item 70 to be tested and inspected can be fixed and attached to the test device in a kind of a hanging configuration above ground or above the base 11. Moreover, the test device 20 itself is located above the hollow breakable item 70. In this way, any splinters or fragments that are produced in the event of breakage of the breakable item 70 simply fall down under the effect of gravity without any detrimental effect on the testing device 20 itself. Arranging the breakable item in a hanging configuration at a lower end of the testing device leaves the testing device substantially unaffected in the event of breakage.

Below the test device 20 there is provided an enclosure 12, typically comprising or forming a container to collect fragments or splinters of the breakable items 70. The enclosure 12 may be displaceable and liftable in longitudinal, hence axial direction, which extends vertically in the various illustrations of FIGS. 1-6. In the present context, an axial distal direction 1 points downwardly whereas an axial proximal direction 2 points upwardly. During a testing procedure, the enclosure 12 featuring an upper opening 13 may be lifted to such an extent, that it effectively encloses and surrounds the breakable item 70 in a contactless way. Splinters or fragments that result from the testing procedure will then be safely collected inside the enclosure 12, thereby preventing an uncontrolled scattering and distribution of splinters and fragments to the environment.

In the illustration according to FIG. 1, the enclosure 12 is lowered so as to provide access to the test device 20, in particular to assemble and to fix a hollow breakable item 70 to the test device 20.

Figures 2, 3:
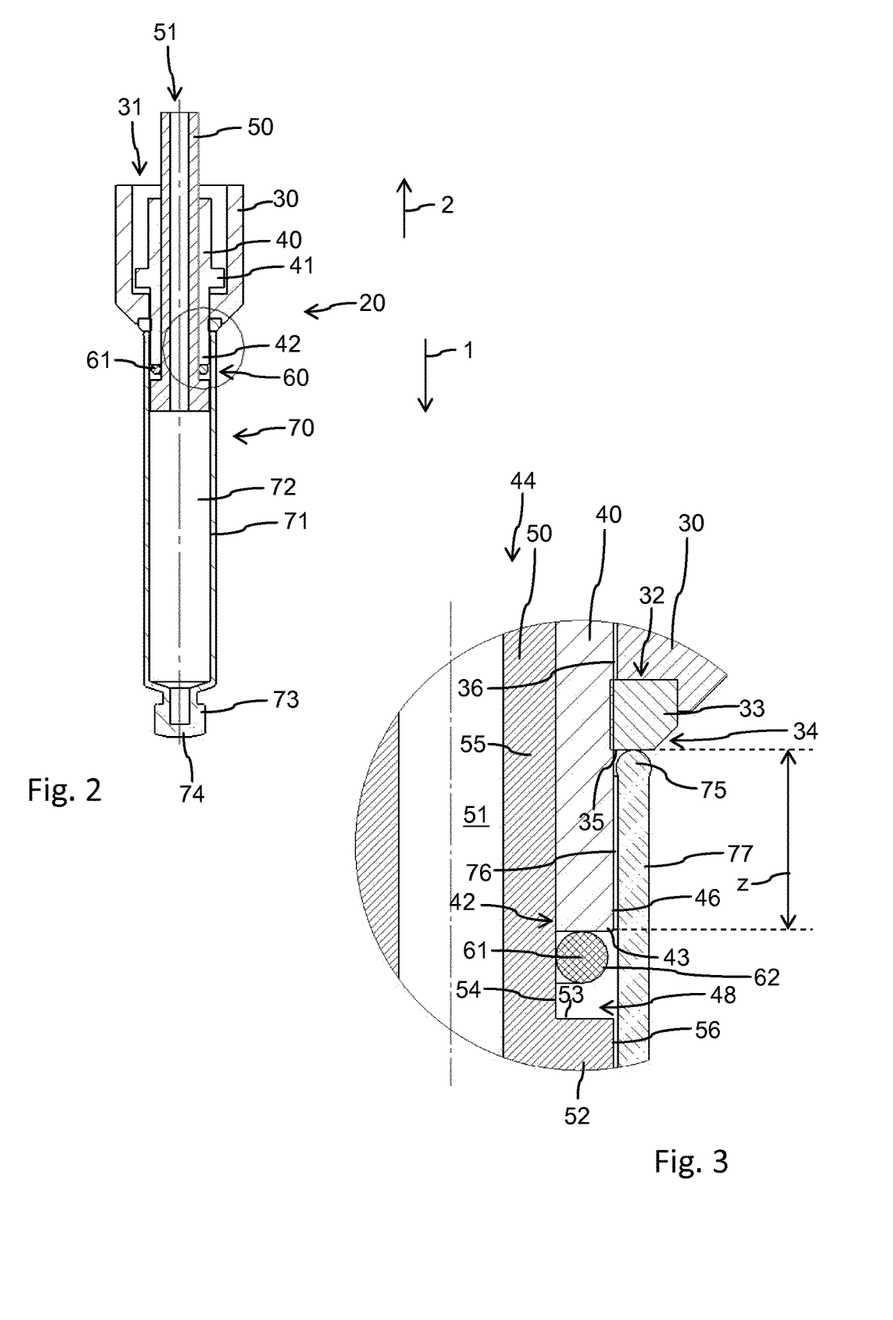
FIG. 2 shows the testing device in cross-section with a breakable item attached thereto.
FIG. 3 shows an enlarged section of the testing device according to FIG. 2 with the squeezable element in an initial relaxed state.

As it is further indicated in FIG. 1, the test device 20 comprises an actuator 21, typically in form of an electric or hydraulic drive. By means of the actuator, a plunger 50 as shown in FIGS. 2 and 3 is displaceable in axial direction, in particular in axial-proximal direction 2 relative to a sleeve 40 that is axially fixed to the test device 20 and hence to the mount 16 thereof.

Additionally, the testing device 20 comprises a force sensor 22 and a displacement sensor 24. The testing device 20 also comprises a control 24 by way of which the displacement of the plunger 50 and hence operation of the actuator 21 is controllable. Additionally, the control 24 is also connected in a data transferring and data processing way with the force sensor 22 and with the displacement sensor 23 in order to monitor a force-displacement path diagram during a testing procedure. The control 24 is typically equipped with a memory as well as with a processor to locally process the sensor signals provided by the force sensor 22 and the displacement sensor 23.

Additionally or alternatively, the control may comprise communication means, in form of wired or wireless connectors by way of which the measured sensor data can be transferred to a further data processing entity, such like a personal computer that is connected with the testing device. Instead of a local control 24, the testing device 20 may be connectable or connected to an external data processing entity that serves to control the actuator 21 and that is operable to process data collected by the force sensor 22 and/or displacement sensor 23. Accordingly, the testing device 20 comprises a connector 17 by way of which control and sensor data can be transferred from and to the testing device 20. The testing device further comprises a housing 18 to accommodate at least one of the sensors 22, 23, the control 24 and the actuator.

Additionally or alternatively, the connector 17 may comprise a hydraulic or vacuum port, by way of which an externally-generated driving force for the actuator 21 can be transferred to the testing device 20. If implemented as a vacuum port, a vacuum generator, such like a vacuum pump or the like can be connected to the testing device 20 via the connector 17, e.g. in order to generate a vacuum or a negative pressure in the interior volume 72 of the breakable item 70.

In FIG. 2, the testing device 20 is shown in more detail. The testing device 20 comprises a holder 30 having a through opening 31 at a lower distal end, a sleeve 40 and a plunger 50 that are arranged in a nested configuration both extend through the lower through opening 31 of the holder and hence extend in distal direction 1 from the lower end of the holder 30. As shown in detail in FIG. 3, the holder 30 comprises an annular recess 32 at a border of the through opening 31. The recess 32 or a respective groove is adapted to receive and/or to form an abutment 34 for the proximal end 75 of the breakable item 70 as shown in FIG. 3. Typically, the abutment 34 comprises an abutment surface 35 against which the proximal end 75 of the breakable item 70 axially extends and abuts in proximal direction 2.

The abutment 34 comprises a sealing member 33 and hence comprises an elastic sealing material so that the proximal circumference of the tubular-shaped breakable item 70 is attachable against the sealing member 33 in a gas- and fluid-tight configuration.

As it is further illustrated in FIG. 3, the abutment 34, hence the sealing member 33 also slightly extends radially-inwardly into the through opening 31 of the holder 30 and slightly extends from an inner surface 36 of the holder's 30 through opening 31. In this way, the sealing member 33 also radially engages with the outer surface 46 of the sleeve 40 extending through the holder 30. Hence, the sealing member 33 also acts as a seal between the holder 30 and the sleeve 40. The sealing member 33 is of annular shape and comprises a cross-section in a ring portion that matches and corresponds to the shape and geometry of the holder's recess 32.

In addition, the sealing engagement between the sleeve 40 and the sealing member 33 also serves as a kind of axial fixing for the sleeve 40 to the holder 30. By way of the sealing member 33, the sleeve 40 is axially fixable to the holder 30 by way of friction. Additionally or alternatively it is also conceivable, that the sleeve 40 is to the holder 30, e.g. by means of a radially-outwardly extending protrusion 41 that may engage with corresponding fixing means (not illustrated) provided in the interior of the holder 30.

The axial position (z) of the sleeve 40 relative to the holder 30 is adjustable as indicated in FIG. 3. Typically, the axial position is continuously adjustable in order to modify an axial distance s between a distal end 42 of the sleeve 40 and the abutment surface 35 of the abutment 34 or sealing member 33. The distance s determines the axial position or axial region of the breakable item's 70 sidewall 77 that is subject to mechanical load to be induced by squeezing of a squeezable element 60 located at the distal end 42 of the sleeve and/or being in axial abutment with the distal end 42 or with a respective contact surface 43 of the sleeve 40.

The sleeve 40 is of hollow shape and comprises a through opening 44 or a respective bore through which a plunger 50 axially extends. The plunger 50 displaceable relative to the sleeve 40 in axial direction is operably connected to the actuator 21. The plunger 50 comprises a longitudinal and tubular or cylindrically-shaped shaft portion 55 whose outer diameter corresponds to and matches with the inner diameter of the sleeve's 40 through opening 44. In this way, the plunger 50 is axially guided by the sleeve 40. At its lower distal end the plunger 50 comprises a radially-widened head portion 52 having an outer diameter that substantially equals the outer diameter of the sleeve 40. Hence, the outer surface 46 of the sleeve 40 and the outer surface 56 of the head portion 52 axially flush.

The radially-widened head portion 52 of the plunger 50 comprises a second contact surface 53 that faces or points in proximal direction 2. Hence, the surface normal of the second contact surface points in proximal direction 2 while the surface normal of the first contact surface 43 located at a distal end 42 of the sleeve 40 points in distal direction 1. In this way, the proximal end of the plunger's 50 head 52 and the distal end 42 of the sleeve 40 form a gap 48 of variable axial size. The size of this gap 48 is variable by displacing the plunger 50 in longitudinal or axial direction relative to the sleeve 40. In this gap 48 and hence axially between the first contact surface 43 and the second contact surface 53 there is arranged a squeezable element 60.

As indicated in FIG. 2, the squeezable element 60 comprises an elastic ring and is hence of annular shape. The cross-section of a portion of the ring of the squeezable element 60 is of circular shape in an initial non-squeezed configuration as shown in FIG. 3. As it is further indicated there, the diameter of the squeezable element 60, hence the inner ring diameter of the squeezable element 60 substantially matches with the outer diameter of the plunger's 50 shaft portion 55. As it is shown in FIG. 3, the radially-inwardly facing portion of the squeezable element 60 is in direct contact with the outer surface 54 of the plunger's 50 shaft portion 55. In this way, the squeezable element 60 can be at least slightly frictionally engaged with the shaft portion 55.

As shown in FIG. 2, the plunger 50 comprises an axial bore 51 that extends all the way through the shaft portion 55 as well as through the head portion 52. In this way, the bore 51 is in fluid communication with the interior volume 72 of the breakable item 70, in particular of its tubular-shaped barrel 71. In the present embodiment, the breakable item 70 comprises a vitreous cartridge featuring a glass barrel 71 that has a stepped down neck portion and a correspondingly-shaped head 73 at its distal and lower end which is further provided with a seal 74. The breakable item 70, hence its barrel 71 may be sealed by a breakable seal 74 or by a pierceable seal 74 depending on the intended purpose for administering the medicament located therein.

By applying a negative pressure or a vacuum to the bore 51 a suction effect can be generated by way of which the breakable item 70 can be kept in axial abutment with the abutment 34 of the holder 30. In this way, a substantially forceless and radially floating fixing of the breakable item 70 to the holder 30 can be attained. The vacuum or negative pressure can be applied through the connector 17 to the central bore 51 of the plunger 50.

Figure 4:
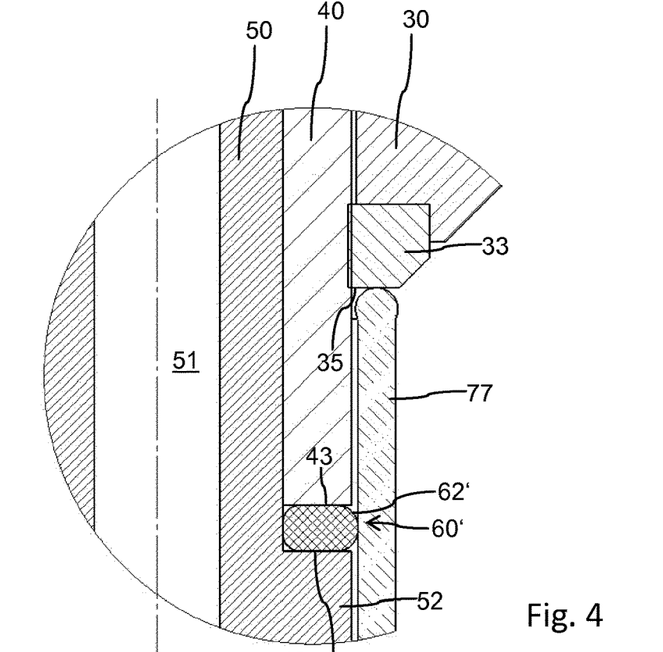
FIG. 4 shows the portion of the testing device according to FIG. 3 wherein the squeezable element is squeezed to a medium extent.
Figure 5:
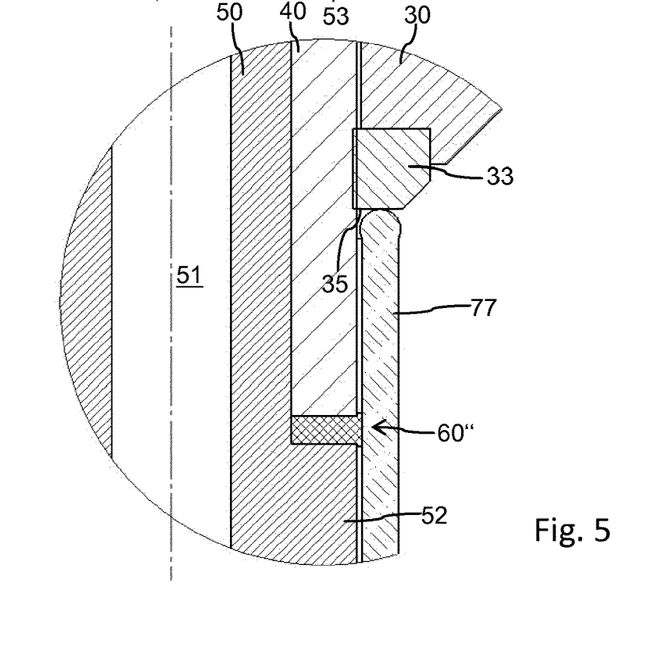
FIG. 5 shows the arrangement according to FIGS. 3 and 4 with the squeezable element squeezed to a large extent and FIG. 6 shows the arrangement according to FIGS. 3-5 with the squeezable element squeezed to such an extent that the breakable item is subject to breakage, FIG. 7 schematically shows a force-displacement path diagram.

Alternatively it is also conceivable, that the breakable item 70 is manually kept in an abutment position as shown in FIG. 3 until the squeezable element 60 is squeezed to such a degree that the breakable item 70 is axially fixed through a friction effect with the slightly radially expanded squeezable element 60' as indicated in FIG. 4. In any case it is of particular benefit, that the breakable item is axially fixed in a radially floating configuration until the squeezable element 60 is squeezed to such an extent that it homogeneously contacts the inner face 71 of the breakable item's 70 sidewall 77.

An axial squeezing of the squeezable element 60 is attained by displacing the plunger 50 in proximal direction 2 relative to the sleeve 40. In this way, the axial size of the gap 48 decreases and the squeezable element 60 is forced to expand radially-outwardly as it becomes apparent from the medium squeezed configuration of the squeezable element 60' according to FIG. 4 and in the rather extreme squeezed configurations of the squeezable element 60" according to FIGS. 5 and 6. While in the relaxed state the outer circumference 62 of the squeezable element 60 is located recessed compared to the outer surfaces 46, 56 of sleeve 40 and plunger 50, respectively the outer circumference 62 of a stressed and squeezed squeezable element 60', 60" radially protrudes from the outer surfaces 46, 56, of sleeve 40 and plunger 50. The axial squeezing of the squeezable element 60 leads to a substantial radially-outwardly directed expansion thereof until the outer circumference 62' of the squeezable element 60 radially protrudes from the outer surfaces 46, 56 of sleeve 40 and plunger 50.

Depending on the elastic or deformation characteristics of the squeezable element 60 and the material it is made of a particular axial-radial pressure transfer function can be provided by the squeezable element 60. Moreover, since the general geometries of the squeezable element 60 and the breakable item 70 mutually match a rather homogeneous mechanical load and pressure can be induced and provided to the sidewall 77 of the breakable item 70. In particular, the entire outer circumference 62' of the squeezable element 60 gets completely in contact with the inner surface 76 of the breakable item's 70 sidewall 77. Moreover, due to the elastic or deformation characteristics of the squeezable element 60, an axially applied pressure acting on the squeezable element 60 is inherently transferred and homogeneously distributed all over the outer circumference 62 of the squeezable element 60. In this way, and as seen in tangential direction a rather homogeneous and well-defined radially-outwardly directed pressure can be induced into the sidewall 77 of the breakable item 70. In this way, precision and reproducibility of successive testing procedures can be increased.

Figure 11:
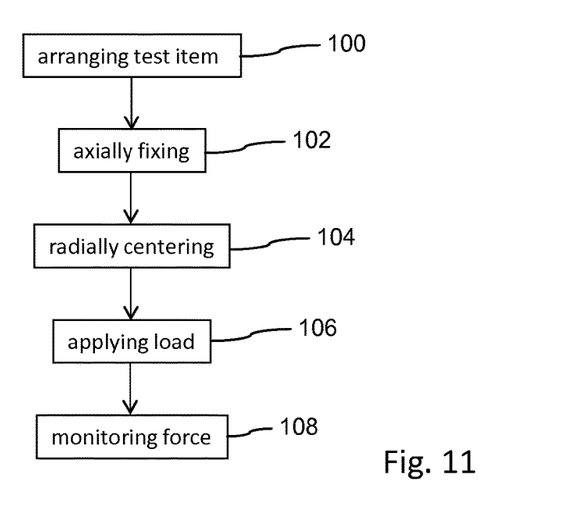
FIG. 11 is indicative of a flowchart of the method of testing the mechanical integrity of the hollow breakable item.

The general testing procedure is conducted as follows and as it is schematically indicated in FIG. 11. In a first step 100 the breakable item 70 is arranged to the testing device 20. The proximal end 75 of the barrel 71, which is open and which is hence accessible for the arrangement of sleeve 40 and plunger 50, is put over the nested arrangement of sleeve 40 and plunger 50 until the proximal end 75, typically exhibiting a slightly bulged rim, axially abuts against the abutment surface 35 of the holder's 30 abutment 34 as it is for instance illustrated in FIG. 3.

In a proceeding step 102, the breakable item 70, i.e. the barrel 71, is axially fixed to the holder 30 and hence to the sleeve 40 and/or plunger 50 either manually or by applying a vacuum or a negative pressure inside the barrel 71. In any case, the barrel 71 is kept in a well-defined axial position, in which it is floatable, hence shiftable or displaceable in radial direction (r), comparatively free of forces so as to center the mutual arrangement of breakable item 70 and the radially-outwardly expandable squeezable element 60. Hence, in step 104 a radial centering and radial floating displacement of the breakable item 70 takes place under the effect of a continuously radially-outwardly expanding squeezable element 60, e.g. until a medium squeezed configuration 60' of the squeezable element 60 has been reached in which the complete and entire outer radial circumference 62 of the squeezable element 60 contacts the inner face 76 of the sidewall 77 of the barrel 71.

As soon as such a configuration has been reached, the breakable item 70 with its barrel 71 is axially fixed to the holder 30, the sleeve 40 and the plunger 50 by way of the radially-expanded squeezable element 60 through a friction effect. Any further axial fixing means may then be deactivated. In particular in the event of applying a vacuum or negative pressure, the interior volume 72 of the barrel 71 may return to atmospheric pressure in order to counteract and prevent contamination of the bore 51 by splinters or fragments when the squeezable element 60 becomes subject to breakage or fracture.

Thereafter in step 106 the axial pressure acting on the squeezable element 60 is continuously increased so as to increase the degree of radial expansion of the squeezable element 60. For this, the plunger 50 is driven further in proximal direction 2 in order to further decrease the axial size of the gap 48. Consequently, the squeezable element 60 continuously develops a radially-outwardly bulging portion that acts on the sidewall 77 of the barrel 71 with increasing forces and mechanical load.

Figure 6:
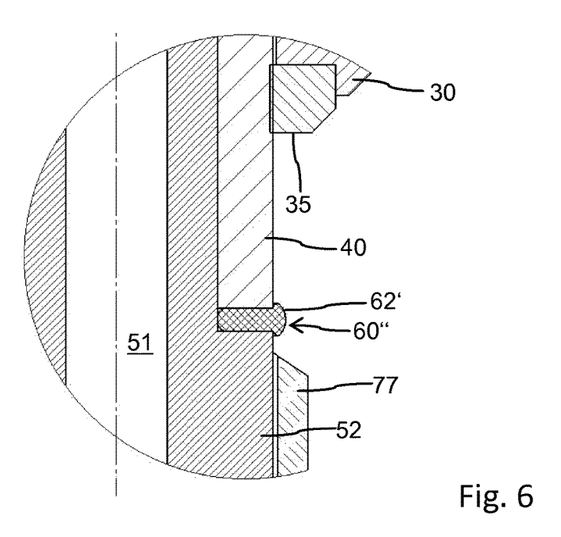

In typical implementations of the testing method and the respective testing procedure the axial pressure onto the squeezable element 60 is increased to gradually and to continuously increase its radial expansion until the breakable item 70 is actually subject breakage, which is schematically illustrated in FIG. 6. Prior to increasing the stress and load onto the squeezable element 60 the enclosure 12 is typically lifted so as to enclose at least a major portion of the breakable item 70. In this way the environment of the testing device 20 can be protected against uncontrolled distribution of splinters and fragments.

Figure 7:
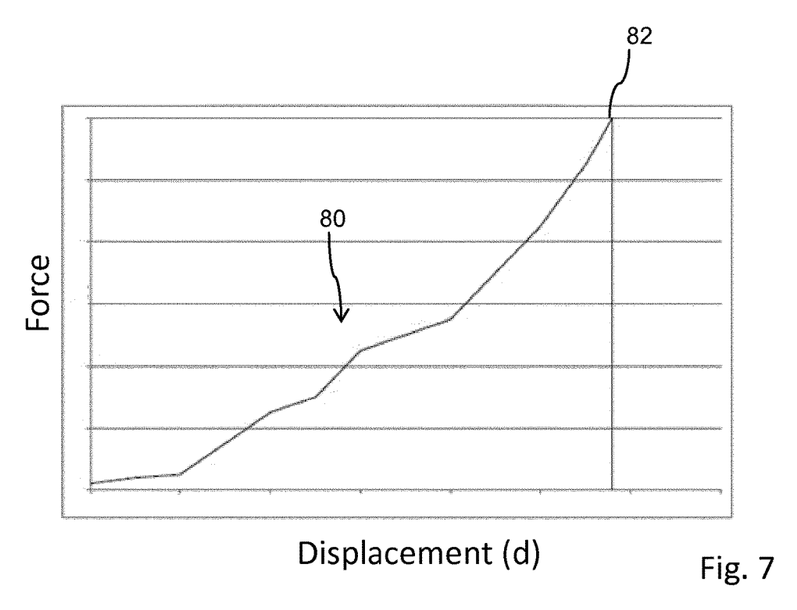

During the gradual or stepwise increase of mechanical load on the squeezable element 60 in step 108 the displacement path of the plunger 50 as well as a driving force acting on the plunger 50 is constantly measured and monitored by way of the force sensor 22 and the displacement sensor 23. Both sensors 22, 23 may also be integrated into the actuator 21. Measurement and monitoring of the applied force versus the axial displacement of the plunger 50 provides force-displacement path diagrams 80 as indicated in FIG. 7. The diagram 80 as shown there exhibits a sharp peak 82 that corresponds to a maximum load that is applicable to the sidewall portion 77 of the breakable item 70. As can be seen at the peak 82, the force present on the plunger 50 abruptly decreases. From the diagram 80, representing numerous discrete measurement values that are connected by straight lines, not only a maximum applicable force but also geometric variations of the barrel 71 can be analyzed and detected in principle. A varying and abruptly changing slope or gradient of the diagram 80 is an indication for the squeezable element 60 actually touching or engaging the inner face 76 of the sidewall 77 of the barrel 71.

Moreover, the dynamics of the relative movement of plunger 50 and sleeve 40 may be modified in order to analyze and/or to test the mechanical integrity of the breakable item 70. The loading rate at which a pressure onto the squeezable element 60 is increased or decreased can be modified according to predefined testing and measurement conditions.

Actually, the force F detectable by the force sensor 22 represents the axial force or load that squeezes the squeezable element 60 in axial direction z. Having knowledge on the specific geometry of the squeezable or squeezing element 60 and the geometry of the gap 48, hence of the first and second contact surfaces 43, 53 the radial load actually acting on the inner surface 76 of the barrel 71 can be either estimated, calculated or determined via experiments. In this way, the measured force F, that may correspond with a respective displacement or displacement path z of the plunger 50 relative to the sleeve 40 can be equally transferred and recalculated into a radially acting load or pressure that is effectively present on the sidewall 77 of the barrel 71 of the breakable item 70.

Figure 8A:
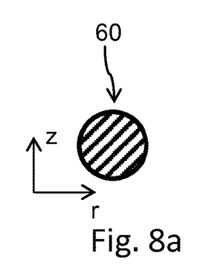
FIGS. 8a-8c illustrate various cross-sections of the ring portion of the squeezable element.
Figure 8B:
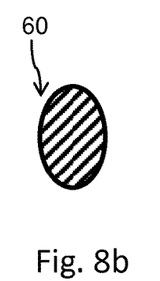
Figure 8C:
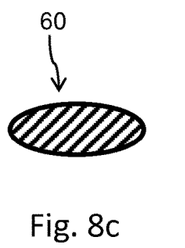

In FIGS. 8a-8c various conceivable cross-sections of ring portions of the squeezable element 60 are indicated. As shown in FIG. 8a, the cross-section of a segment of the squeezable element 60 may comprise a circular shape. In this case, the squeezable element 60 may comprise an elastic ring 61, such like an O-ring. In the embodiment according to FIG. 8b, the cross-section of a segment of the squeezable element 60 is oval and comprises a larger extension in axial direction (z) than in radial direction (r). In FIG. 8c another embodiment of a squeezable element 60 is shown, wherein the cross-section of a segment of the elastic ring 61 is oval with an oval long axis extending in radial direction and with an oval short axis extending in axial direction. The degree of radial deformability and the response to an axial load of squeezable elements 60 according to FIGS. 8b and 8c may drastically differ. Depending on a specific application scenario and a required axial-radial pressure transfer function an appropriate squeezable element 60 may be selected.

Figure 9A:
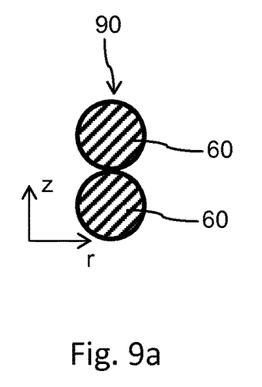
FIGS. 9a-9b show cross-sections through ring portions of several squeezable elements arranged in axial abutment, FIG. 10 schematically illustrates a rectangular-shaped cross-section of a ring portion of the squeezable element

In FIG. 9a an arrangement of at least two squeezable elements 60 is shown in cross-section. There, the arrangement 90 comprises two squeezable elements 60 of substantially identical shape that are attached to each other and abut in axial direction. The outer circumference 62 of each of the squeezable elements 60 axially flush. In practice, making use of an arrangement 90 as shown in FIG. 9a in the gap 48 between the sleeve 40 and the plunger 50 leads to an enlargement of the contact area of the arrangement 90 with the inner surface 76 of the sidewall 77 of the barrel compared to a configuration making use of only one squeezable element 60.

Figure 9B:
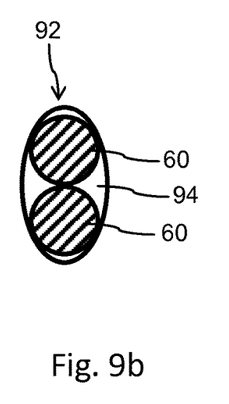

The arrangement 92 as shown in FIG. 9b comprises two annular-shaped squeezable elements 60 that are axially adjacently located and that are further embedded in an outer cladding 94. The cladding 94 not only keeps together the two individual squeezable elements 60 but may provide and exhibit a different elastic behavior compared to the individual squeezable elements 60. Hence, the arrangement 92 can be regarded as a multilayered or multi-component squeezable element. Axial squeezing thereof may lead to a radial expansion thereof that distinctively differs for instance from the radial expansion of a squeezable element 60 as shown in FIG. 8b.

Figure 10:
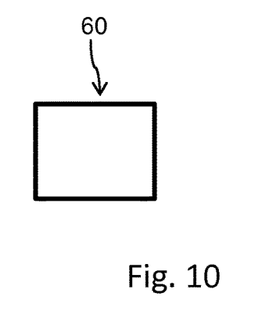

In FIG. 10, a further cross-section of a section of another squeezable element 60 is illustrated. Here, the squeezable element may also be of annular shape but the ring itself is not of circular but of rectangular or quadratic cross-section. This type of squeezable element 60 may also exhibit a totally different radial expansion behavior compared to those squeezable elements 60 as shown in FIG. 8a, 8b or 8c.

LIST OF REFERENCE NUMBERS 1 distal direction
2 proximal direction
10 test station
11 base
12 enclosure
13 opening
14 support
15 crossbar
16 mount
17 connector
18 housing
20 testing device
21 actuator
22 force sensor
23 displacement sensor
24 control
30 holder
31 through opening
32 recess
33 sealing member
34 abutment
35 abutment surface
36 inner surface
36 sleeve
40 protrusion
41 distal end
42 contact surface
44 through opening
46 outer surface
48 gap
50 plunger
51 through opening
52 head portion
53 contact surface
54 outer surface
55 shaft portion
56 outer surface
60 squeezable element
61 elastic ring
62 outer circumference
70 breakable item
71 barrel
72 interior volume
73 head
74 seal
75 proximal end
76 inner surface
77 sidewall
80 diagram
82 peak
90 arrangement
92 arrangement
94 cladding

The invention claimed is:

1. A testing device for testing a mechanical integrity of a hollow breakable item, the testing device comprising:
a squeezable element to radially abut with a sidewall portion of the breakable item;
a sleeve extending in an axial direction to receive the sidewall portion of the breakable item and having a first contact surface to axially engage with the squeezable element; and
a plunger displaceable in the axial direction relative to the sleeve and having a second contact surface to axially engage with the squeezable element,
wherein the squeezable element is axially squeezable by a relative displacement of plunger and sleeve to radially expand the squeezable element and to apply radially directed pressure to the sidewall portion of the breakable item,
wherein the sleeve and the plunger axially extend through a holder having an abutment to axially engage with a proximal end of the breakable item, and
wherein the abutment comprises an annular seal, the seal comprising a distally facing abutment surface configured to abut a proximal end of the breakable item.

2. The testing device according to claim 1, wherein the sleeve comprises an axial through opening through which the plunger extends in the axial direction.

3. The testing device according to claim 1, wherein the plunger comprises an axially extending shaft portion and a head portion at a distal end of the shaft portion, wherein the head portion is radially widened compared to the shaft portion.

4. The testing device according to claim 3, wherein an outer surface of the head portion is configured to be axially flush with an outer surface of the sleeve.

5. The testing device according to claim 3, wherein:
the first contact surface is located at a distal end of the sleeve, and
the second contact surface is located at a proximal face of the head portion of the plunger.

6. The testing device according to claim 1, wherein the squeezable element comprises an elastic ring extending around the plunger, the elastic ring being arranged axially between the first contact surface and the second contact surface.

7. The testing device according to claim 1, wherein:
the sleeve is axially displaceable relative to the holder, and
the sleeve is axially fixable to the holder at variable axial positions.

8. The testing device according to claim 1, wherein the plunger comprises an axial bore to apply a negative pressure to an interior volume of the breakable item.

9. The testing device according to claim 1, further comprising:
an actuator to displace the plunger relative to the sleeve; and
at least one of
a force sensor to determine an axial driving force present on the plunger and
a displacement sensor to determine an axial displacement path of the plunger relative to the sleeve.

10. The testing device according to claim 1, wherein the first contact surface extends along a plane substantially perpendicular to the axial direction.

11. The testing device according to claim 1, wherein the first contact surface and the second contact surface are substantially parallel to one another.

12. The testing device according to claim 1, wherein the breakable item comprises a cartridge to be filled with a medicament.

13. A testing mechanism for testing the mechanical integrity of a hollow breakable item, the testing mechanism comprising:
an expandable element configured to abut a sidewall portion of the breakable item;
first and second axially extending members movable relative to one another along an axial direction to cause the expandable element to expand such that a pressure is applied on the sidewall portion of the breakable item;
a holder having an abutment to axially engage with a proximal end of the breakable item, the abutment comprising an annular seal, and the seal comprising a distally facing abutment surface configured to abut a proximal end of the breakable item; and
at least one of a force sensor and a displacement sensor to measure at least one of a driving force and an axial displacement path between the first and second axially extending members.

14. The testing mechanism according to claim 13, wherein the first axially extending member comprises an axial through opening through which the second axially extending member extends in an axial direction.

15. A method of testing a mechanical integrity of a hollow breakable item, the method comprising the steps of:
arranging the hollow breakable item over an axially extending sleeve of a testing device in a predetermined axial position and bringing a proximal end of the hollow breakable item into abutment with a distally facing abutment surface of an annular seal,
axially displacing a plunger of the testing device relative to the sleeve to axially squeeze a squeezable element between contact surfaces of the sleeve and the plunger to radially expand the squeezable element to such an extent that the squeezable element applies a radially directed pressure to a sidewall portion of the breakable item, and
wherein at least one of
an axial driving force applied to the plunger, and
an axial displacement path of the plunger relative to the sleeve is determined by at least one of a force sensor and a displacement sensor during axial displacement of the plunger relative to the sleeve.

16. The method according to claim 15, wherein the driving force is monitored over the axial displacement path of the plunger until the breakable item is subject to breakage.

17. The method according to claim 15, wherein:
the breakable item is axially fixed to a holder, and
the breakable item is radially centered with regard to at least any one of the sleeve, the plunger, and the holder by the radially expanding squeezable element.

18. The method according to claim 15, further comprising applying a vacuum or negative pressure in an interior volume of the breakable item.

19. The testing device of claim 1, wherein the seal is arranged on an outer surface of the sleeve and is configured to engage with the breakable item.

20. The testing device of claim 19, wherein the seal is configured to contact a circumference of a proximal end of the breakable item.

21. The testing device of claim 1, wherein the plunger comprises a shaft portion extending through a proximal end of the sleeve and through a distal end of the sleeve.

22. The testing device of claim 21, wherein an axial bore extends through a proximal end of the shaft portion and through a distal end of the shaft portion.

* * * * *